(12) United States Patent
Bhattacharyya et al.

(10) Patent No.: US 9,091,659 B2
(45) Date of Patent: Jul. 28, 2015

(54) HYDROLASE DETECTION SYSTEM WITH STERICALLY CAGED SUBSTRATES

(71) Applicants: Sukanta Bhattacharyya, Belmont, CA (US); Daniel Sobek, Portola Valley, CA (US)

(72) Inventors: Sukanta Bhattacharyya, Belmont, CA (US); Daniel Sobek, Portola Valley, CA (US)

(73) Assignee: Zymera, Inc., San Jose, CA (US)

( * ) Notice: Subject to any disclaimer, the term of this patent is extended or adjusted under 35 U.S.C. 154(b) by 0 days.

(21) Appl. No.: 14/022,204

(22) Filed: Sep. 9, 2013

(65) Prior Publication Data

US 2014/0011225 A1   Jan. 9, 2014

Related U.S. Application Data

(63) Continuation-in-part of application No. 12/445,378, filed as application No. PCT/US2007/081697 on Oct. 17, 2007, now Pat. No. 8,530,178.

(60) Provisional application No. 60/829,877, filed on Oct. 17, 2006.

(51) Int. Cl.
| | |
|---|---|
| *C12Q 1/34* | (2006.01) |
| *G01N 21/76* | (2006.01) |
| *G01N 33/542* | (2006.01) |
| *G01N 33/58* | (2006.01) |

(52) U.S. Cl.
CPC ............... *G01N 21/763* (2013.01); *C12Q 1/34* (2013.01); *G01N 33/542* (2013.01); *G01N 33/582* (2013.01)

(58) Field of Classification Search
USPC ....................................................... 435/21, 8
See application file for complete search history.

(56) References Cited

U.S. PATENT DOCUMENTS

| 8,530,178 B2 * | 9/2013 | Sobek et al. .................... 435/21 |
| 2006/0099646 A1 | 5/2006 | Heding |
| 2006/0105915 A1 | 5/2006 | Naleway et al. |
| 2011/0097753 A1 | 4/2011 | Wang et al. |

FOREIGN PATENT DOCUMENTS

WO   0146691 A1   6/2001

OTHER PUBLICATIONS

Frangioni, "Self-illuminating quantum dots light the way", "Nature Biotechnology", Nature Publishing Group, Mar. 2006, pp. 326-328, vol. 24, No. 3.
Hall et al., "Engineered Luciferase Reporter from a Deep Sea Shrimp Utilizing a Novel Imidazopyrazinone Substrate", ACS Chemical Biology, 2012, pp. 1848-1857, vol. 7, Publisher: American Chemical Society.
Huang et al., "A Resonance Energy Transfer Between Chemiluminescent Donors and Luminescent Quantum Dots as Acceptors", Angew. Chem. Int. Ed, 2006, pp. 5140-5143, vol. 45.
Swezey et al., "The in vivo rate of glucose-6-phosphate dehydrogenase activity in sea urchin eggs determined with a photolabile caged substrate", "Developmental Biology", 1995, pp. 733-744, vol. 169.
Xu et al., "A self-assembled quantum dot probe for detecting b-lactamase activity", "Biochemical and Biophysical Research Communications", 2006, pp. 931-935, vol. 344.
Yao et al., "A Bioluminogenic Substrate for In Vivo Imaging of b-Lactamase", "Imaging Probes", Angew. Chem. Int. Ed., 2007, pp. 7031-7034, vol. 46.
Zhang et al., "HaloTag protein-mediated site-specific conjugation of bioluminescent proteins to quantum dots", Agnew Chem. Int., 2006, pp. 4936-4940, vol. 45.

* cited by examiner

*Primary Examiner* — Ralph Gitomer
(74) *Attorney, Agent, or Firm* — Ishimaru & Associates LLP

(57) ABSTRACT

A qualitative and quantitative hydrolase detection method includes providing a caged coelenterazine molecule having a detection molecule bonded between a first bonding site or a second bonding site of a coelenterazine molecule and a steric caging group; activating an uncaged coelenterazine molecule by cleaving the detection molecule in the caged coelenterazine molecule with a hydrolase enzyme; determining a light emission from a coelenterazine-activated bioluminescent enzyme reacting with the uncaged coelenterazine molecule activated in the presence of the hydrolase enzyme; and correlating the light emission for quantitatively and qualitatively determining the presence of the hydrolase enzyme.

20 Claims, 8 Drawing Sheets

HYDROLASE DETECTION SYSTEM WITH STERICALLY CAGED SUBSTRATES

CROSS-REFERENCE TO RELATED APPLICATION(S)

This application is a continuation-in-part of U.S. patent application Ser. No. 12/445,378 filed Apr. 13, 2009, now U.S. Pat. No. 8,530,178, which claims the benefit of is the National Stage of International Application serial number PCT/US2007/081697 filed Oct. 17, 2007, which claims the benefit of U.S. Provisional Patent Application Ser. No. 60/829,877 filed Oct. 17, 2006, and the subject matter thereof is incorporated herein by reference thereto.

TECHNICAL FIELD

The present invention relates to a system of caged substrates suitable for use in biochemical assays and more specifically to an enzyme detection system with caged substrates.

BACKGROUND ART

Enzyme activity measurements are clinical biomarkers for organ or muscle function. The detection principles disclosed in this document can be applied to hydrolases: enzymes that catalyze hydrolysis that results in the cleavage of an enzyme-specific side-group from the rest of the substrate. Examples include alkaline phosphatase (ALP), cholinesterase, and, esterase. ALP measurements are discussed in detail to illustrate the general detection method which may be applied for any of the mentioned enzymes. ALP is an enzyme included in standard liver panel assays and is a marker of cholestatic hepatoxicity. A higher than normal level of ALP may indicate that the subject of the test has liver disease, or cancer of the liver or bones.

Existing ALP assays measure enzyme activity using a chromogenic substrate consisting of 4-nitrophenyl phosphate. The chromogenic substrate, placed in an alkaline environment, changes to a yellow color in the presence of ALP. The color change is quantified by measuring the absorption spectrum using a spectrophotometer. Enzyme activity in chromogenic assays depends upon the reagent buffer's ability to revitalize the enzyme, pH, and the preservation of the blood specimen. Additional disadvantages of chromogenic assays are the production of precipitates that may interfere with enzyme activity thereby reducing sensitivity.

The chromogenic assays may be further complicated by interference caused by quenching from hemoglobin in red blood cells. This level of interference may reduce the sensitivity of chromogenic assays and possibly mask the presence of some low level enzymes.

Thus, a need still remains for an enzyme detection system with caged substrates that may improve the efficiency of whole blood assays. In view of the aging world population, it is increasingly critical that answers be found to these problems. With extended life expectancy and the development of many new drugs to support it, an efficient and cost effective enzyme detection system is a primary concern. Additionally, the need to save costs, improve efficiencies and performance, and meet competitive pressures, adds an even greater urgency to the critical necessity for finding answers to these problems.

Solutions to these problems have been long sought but prior developments have not taught or suggested any solutions and, thus, solutions to these problems have long eluded those skilled in the art.

DISCLOSURE OF THE INVENTION

The present invention provides an enzyme detection method including forming a caged substrate; releasing an uncaged substrate by cleaving a caging molecule from the caged substrate; and emitting a light emission from a Bioluminescence Resonance Energy Transfer luminescent nanocrystal conjugate reacting with the uncaged substrate.

The present invention provides an enzyme detection system including a caged substrate; an uncaged substrate released by a caging molecule cleaved from the caged substrate; and a light emission from a Bioluminescence Resonance Energy Transfer luminescent nanocrystal conjugate from the uncaged substrate reaction.

Certain embodiments of the invention have other aspects in addition to or in place of those mentioned above. The aspects will become apparent to those skilled in the art from a reading of the following detailed description when taken with reference to the accompanying drawings.

BEST MODE FOR CARRYING OUT THE INVENTION

Figure 1A:
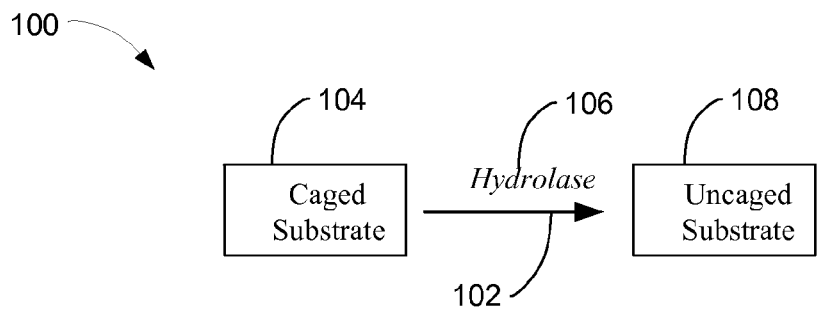
FIGS. 1A and 1B are a reaction diagram of a generalized assay for measuring hydrolase activity in whole blood, in an embodiment of the present invention.

The following embodiments are described in sufficient detail to enable those skilled in the art to make and use the invention. It is to be understood that other embodiments would be evident based on the present disclosure, and that process or mechanical changes may be made without departing from the scope of the present invention.

In the following description, numerous specific details are given to provide a thorough understanding of the invention. However, it will be apparent that the invention may be practiced without these specific details. In order to avoid obscuring the present invention, some well-known system configurations and process steps are not disclosed in detail. Likewise, the drawings showing embodiments of the system are semi-diagrammatic and not to scale and, particularly, some of the dimensions are for the clarity of presentation and are shown greatly exaggerated in the drawing FIGS. Where multiple embodiments are disclosed and described, having some features in common, for clarity and ease of illustration, description, and comprehension thereof, similar and like features one to another will ordinarily be described with like reference numerals.

For expository purposes, the term "horizontal" as used herein is defined as a plane parallel to the plane or contact surface of the platform, regardless of its orientation. The term "vertical" refers to a direction perpendicular to the horizontal as just defined. Terms, such as "above", "below", "bottom", "top", "side" (as in "sidewall"), "higher", "lower", "upper", "over", and "under", are defined with respect to the horizontal plane. The term "on" means there is direct contact among elements. The term "system" as used herein means and refers to the method and to the apparatus of the present invention in accordance with the context in which the term is used.

Figure 1B:
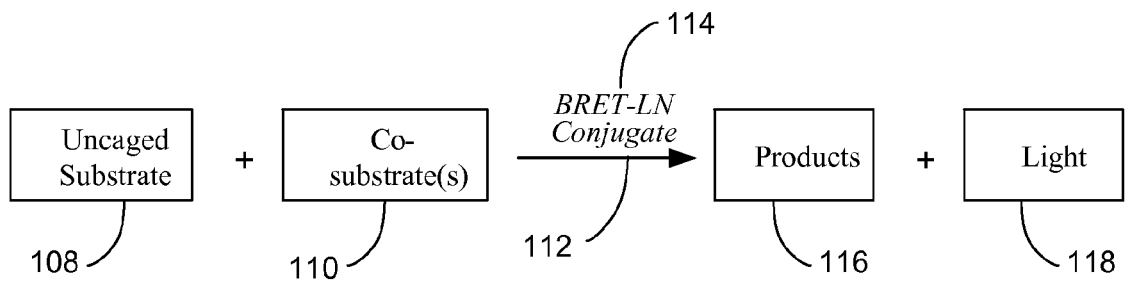

Referring now to FIGS. 1A and 1B, therein is shown a reaction diagram of a generalized assay for hydrolase 100 activity in whole blood, in an embodiment of the present invention. The reaction diagram of the generalized assay for hydrolase 100 depicts a first reaction 102 including a caged substrate 104. A caged substrate 104 is defined as the substrate for a bioluminescent molecule such as *Renilla* luciferase with a cleavable caging group that may be cleaved by the action catalyzed by a hydrolase enzyme 106. Hydrolases catalyze the hydrolysis of a chemical bond. The caged substrate 104 is not active as a substrate for a bioluminescent reaction. Once the caging group is removed by the hydrolase enzyme 106, the resulting uncaged substrate 108, is active as a substrate for the bioluminescent reaction.

Referring now to FIG. 1B, therein is shown the reaction diagram of the generalized assay for hydrolase 100. The reaction diagram of the generalized assay for hydrolase 100 depicts the uncaged substrate 108 combined with a co-substrate 110 and in a reaction 112 catalyzed by a Bioluminescence Resonance Energy Transfer luminescent nanocrystal (BRET-LN) conjugate 114. The BRET-LN conjugate 114 may include a luminescent nanocrystal (not shown) that may be made by linking *Renilla* luciferase (not shown) to a semiconductor nanostructure (not shown). The reaction 112 produces products 116 and a light emission 118 from the BRET-LN conjugate 114.

The BRET-LN conjugate 114 enables the light emission 118 in a wave length ranging from 600 nm to 900 nm. This range encompasses the red visible spectrum and the near infrared spectrum. The light emission 118 in this range of wavelengths may emit without significantly being quenched by hemoglobin in the blood or exciting autofluorescence from the blood proteins. This aspect of the invention allows highly sensitive assays without the requirement of separating the red cells from the blood.

Figure 2:
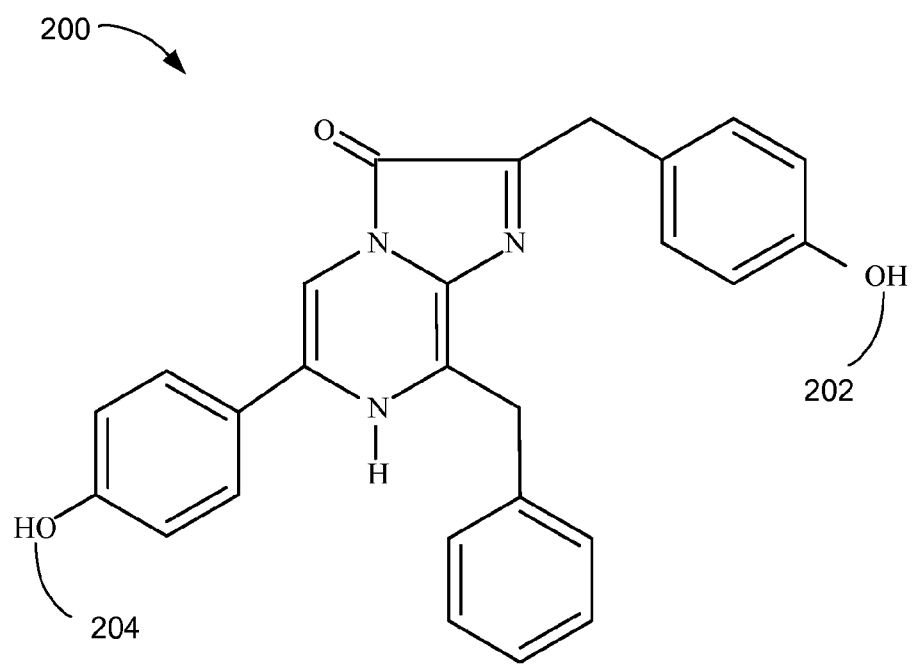
FIG. 2 is a bonding diagram of a coelenterazine molecule, having two positions where a caging group may be attached.

Referring now to FIG. 2, therein is shown a bonding diagram of a coelenterazine molecule 200, having two positions where a caging group may be attached. The bonding diagram of the coelenterazine molecule 200 depicts a first bonding site 202 and a second bonding site 204. The first bonding site 202 and the second bonding site 204 include hydroxyl groups. The coelenterazine molecule 200 may act as a substrate for activating *Renilla* luciferase (not shown) to produce the light emission 118, of FIG. 1.

Figure 3:
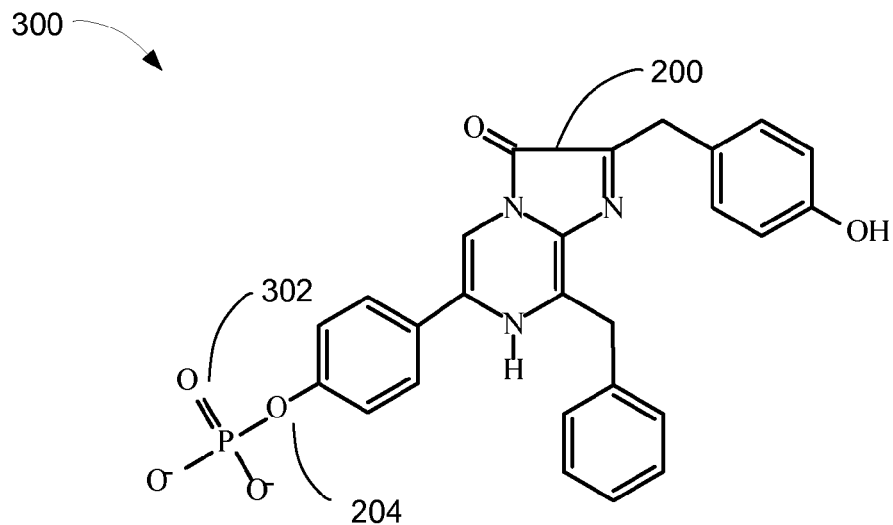
FIG. 3 is a bonding diagram of a caged coelenterazine molecule, having a phosphate group attached.

Referring now to FIG. 3, therein is shown a bonding diagram of a caged coelenterazine molecule 300, having a phosphate group attached. The bonding diagram of the caged coelenterazine-phosphate molecule 300 depicts the coelenterazine molecule 200 having a caging molecule 302, such as a phosphate group, bonded to the second site 204. The caging molecule 302 replaces the hydroxyl group of the first bonding site 202 or the second bonding site of FIG. 2. The caged coelenterazine-phosphate molecule 300 is no longer capable of acting as a substrate for activating *Renilla* luciferase (not shown) to produce the light emission 118, of FIG. 1. As long as the caging molecule 302 is present the coelenterazine molecule 200 cannot perform as a substrate to activate any luminescent enzyme. The caged coelenterazine-phosphate molecule 300 is also known as a caged substrate.

Figure 4A:
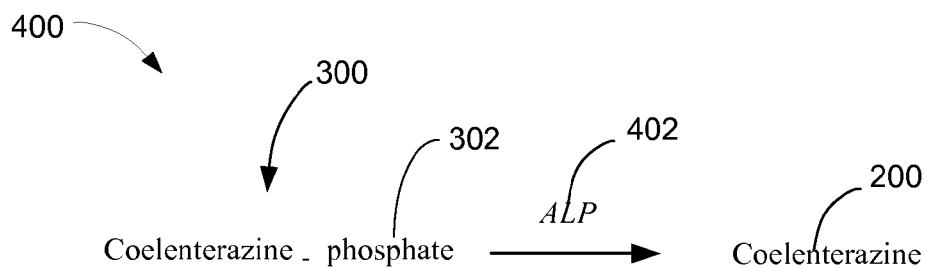
FIGS. 4A and 4B are a reaction diagram of an enzyme detection system with caged substrates, using the coelenterazine molecule, in an embodiment of the present invention.
Figure 4B:
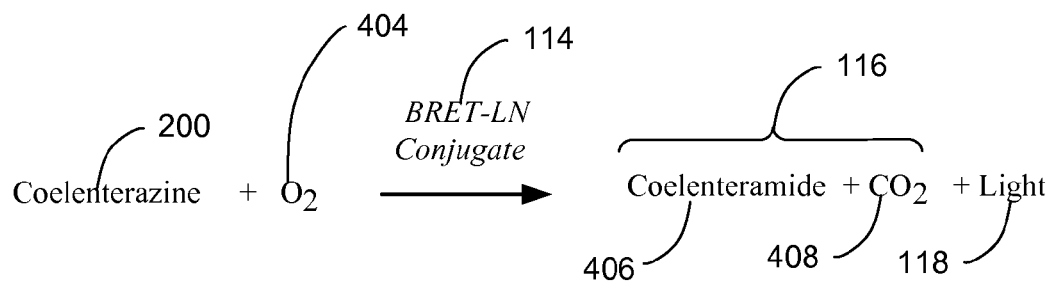

Referring now to FIGS. 4A and 4B, therein are shown a reaction diagram of an enzyme detection system 400 with caged substrates, using the coelenterazine molecule, in an embodiment of the present invention. The reaction diagram of FIG. 4A depicts the enzyme detection system 400 with caged substrates, including the caged coelenterazine-phosphate molecule 300. An alkaline phosphatase (ALP) molecule 402 catalyzes the cleavage of the caging molecule 302 and restores the coelenterazine molecule 200. In this reaction the limiting substance will be the alkaline phosphatase (ALP) molecule 402. Only a portion of the caged coelenterazine-phosphate molecules 300 will be cleaved by the alkaline phosphatase (ALP) molecules 402. The portion that is cleaved will be free to react in the next reaction as displayed in FIG. 4B. The remaining molecules of the caged coelenterazine-phosphate molecule 300 will remain inert in the reaction.

Referring now to FIG. 4B, therein is shown a reaction diagram of the enzyme detection system 400 with caged substrates. The reaction diagram of the enzyme detection system 400 depicts the coelenterazine molecule 200 that is in solution with an oxygen ($O_2$) molecule and catalyzed by the BRET-LN conjugate 114. The products 116 of the reaction include a coelenteramide molecule 406 and a carbon dioxide ($CO_2$) molecule 408. The light emission 118 will be correlated to the number of the coelenterazine molecule 200 that were liberated during the reaction of FIG. 4A. The amount of the light emission 118 will be indicative of the activity of the alkaline phosphatase (ALP) molecules 402 from the reaction of FIG. 4A.

Figure 5:
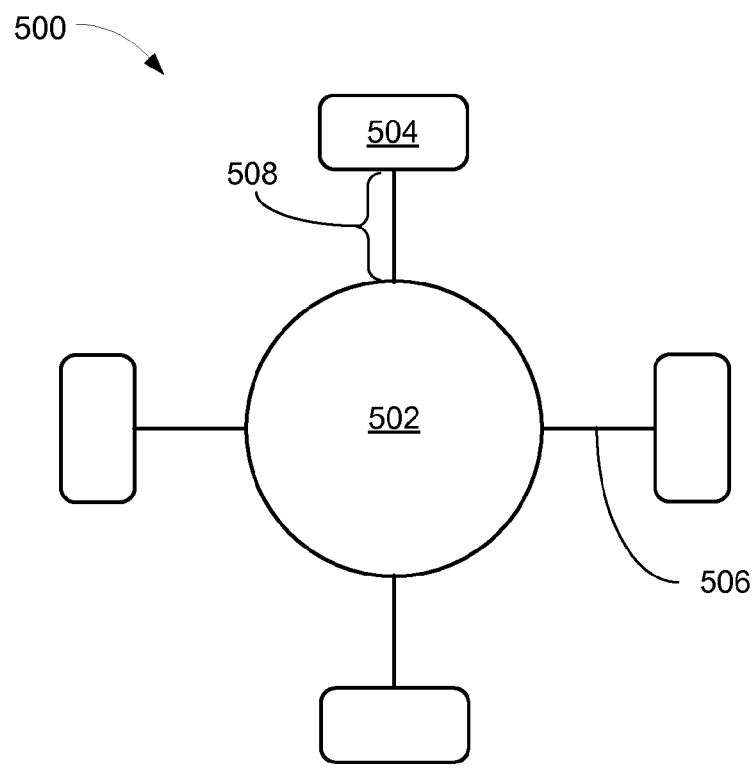
FIG. 5 is a block diagram of a Bioluminescence Resonance Energy Transfer luminescent nanocrystal (BRET-LN) conjugate, in an embodiment of the present invention.

Referring now to FIG. 5, therein is shown a block diagram of a Bioluminescence Resonance Energy Transfer luminescent nanocrystal (BRET-LN) conjugate 500, in an embodiment of the present invention. The block diagram of the BRET-LN conjugate 500 depicts a semiconductor nanostructure 502, such as a bioluminescent resonance energy transfer acceptor molecule, linked to a luminescent enzyme 504, such as a bioluminescent enzyme or a chemiluminescent enzyme acting as a bioluminescent resonance energy transfer donor molecule. The luminescent enzyme 504 may be held in position by a spacing molecule 506. The luminescent enzyme 504 must be held within a Foster distance 508, usually between 10 and 100 Angstrom, in order to allow the Bioluminescent Resonant Energy Transfer to take place.

In an example of the luminescent nanocrystal 500, the semiconductor nanostructure 502 may be linked, at the Foster distance 508 of 30 Angstroms, to the luminescent enzyme 504, such as a *Renilla* luciferase, that may emit at a wavelength of 480 nm. When the luminescent nanocrystal 500 is activated, the luminescent enzyme 504 will activate the semiconductor nanostructure 502 through the Bioluminescent Resonance Energy Transfer. The semiconductor nanostructure 502 may be formulated to provide the light emission 118, of FIG. 1, at a wavelength of 600 nm to 900 nm In the previous example, the use of Bioluminescent Resonance Energy Transfer (BRET) conjugates composed of the luminescent nanocrystal 500 such as the semiconductor nanostructure 502 closely linked to the luminescent enzyme 504 that employs the adenosine triphosphate (ATP) molecule (not shown) as a co-substrate, such as the *Renilla* luciferase. In the preferred implementation of the invention, the BRET-LN conjugate 500 would incorporate a mutant form of the luminescent enzyme 504 optimized for maximum stability.

In a preferred embodiment of the invention the semiconductor nanostructure 502 that may emit in the red visible light spectrum will be used as a BRET acceptor molecule. Emissions at wavelengths longer than 650 nm minimize the possibility of exciting autofluorescence of blood proteins such as hemoglobin.

There are many ways to achieve a stable linkage between the semiconductor nanostructure 502 and the luminescent enzyme 504. One method is to form a stable amide linkage between the two molecules using 1-ethyl-3-(3-dimethylaminopropyl) carbodiimide hydrochloride (EDC) as a coupling reagent. A second method that has the potential to better retain the activity of the luminescent enzyme 504 is to add a histadine tag to the luminescent enzyme 504, and conjugate nickel-nitrilotriacetate (NTA) to the semiconductor nanostructure 502 in the presence of nickel ions. A third method involves using a streptavidin-biotin bond, with streptavidin on the surface of the semiconductor nanostructure 502 and biotin-conjugated with the luminescent enzyme 504. There are many other methods that could be employed to create the BRET-LN conjugate incorporating Luciferin.

Figure 6:
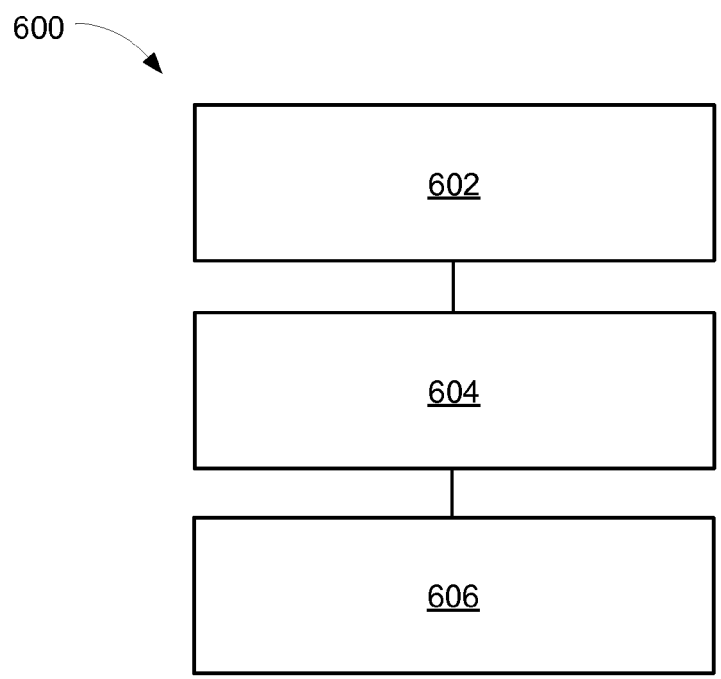
FIG. 6 is a flow chart of an enzyme detection system for operating the enzyme detection system with caged substrates, in an embodiment of the present invention.

Referring now to FIG. 6, therein is shown a flow chart of an enzyme detection system 600 for operating the enzyme detection system with caged substrates, in an embodiment of the present invention. The system 600 includes forming a caged substrate in a block 602; releasing an uncaged substrate by cleaving a caging molecule from the caged substrate in a block 604; and emitting a light emission from a Bioluminescence Resonance Energy Transfer luminescent nanocrystal conjugate reacting with the uncaged substrate in a block 606.

It has been discovered that the present invention thus has numerous aspects.

The invention is the specific modification of the coelenterazine molecule at either of two potential attachment points containing a hydroxyl molecule. The covalent addition of an enzyme-cleavable molecule, such as a phosphate group, to either of this attachment points inactivates coelenterazine as a substrate for the reaction catalyzed by *Renilla* luciferase. The enzyme-cleavable group is chosen for specificity to a given enzyme, for example, a phosphate group for specificity to alkaline phosphatase (ALP), which may be present in a whole blood sample. Cleavage of the added group due to the catalytic action of the enzyme of interest, such as the alkaline phosphatase (ALP), activates the coelenterazine as a substrate for the reaction catalyzed by *Renilla* luciferase, creating light emission, such as a bioluminescent light output, that can be correlated to the presence and activity of the cleaving enzyme. In this example the cleaving enzyme may be alkaline phosphatase (ALP).

A principle aspect that has been unexpectedly discovered is that the present invention is that the inventive hydrolase assays may be implemented as homogeneous or heterogeneous assays in open platform such as well-plate readers or high-throughput clinical chemistry analyzers, or in microfluidic format or microarray format. When implemented as a heterogeneous assay, the BRET-LN conjugate is immobilized on a surface directly or linked to the surface through n spacer arm. The surface material may be glass, noble metals, thin-film dielectrics, ceramics, plastics, and any other material that that can be functionalized to provide a chemical link between the surface and a luminescent nanocrystal. The surface-linked BRET-LN conjugates may be surrounded by pegylated surfaces or any other anti-fouling film that prevents non-specific binding.

Another important aspect of the present invention is that it valuably supports and services the historical trend of reducing costs, simplifying systems, and increasing performance.

These and other valuable aspects of the present invention consequently further the state of the technology to at least the next level.

Thus, it has been discovered that the enzyme detection system with caged substrates of the present invention furnishes important and heretofore unknown and unavailable solutions, capabilities, and functional aspects for detecting the measurement of Alkaline Phosphatase (ALP) activity in whole blood. The resulting processes and configurations are straightforward, cost-effective, uncomplicated, highly versatile and effective, can be surprisingly and unobviously implemented by adapting known technologies, and are thus readily suited for efficiently and economically manufacturing enzyme analysis devices fully compatible with conventional manufacturing processes and technologies.

Figure 7:
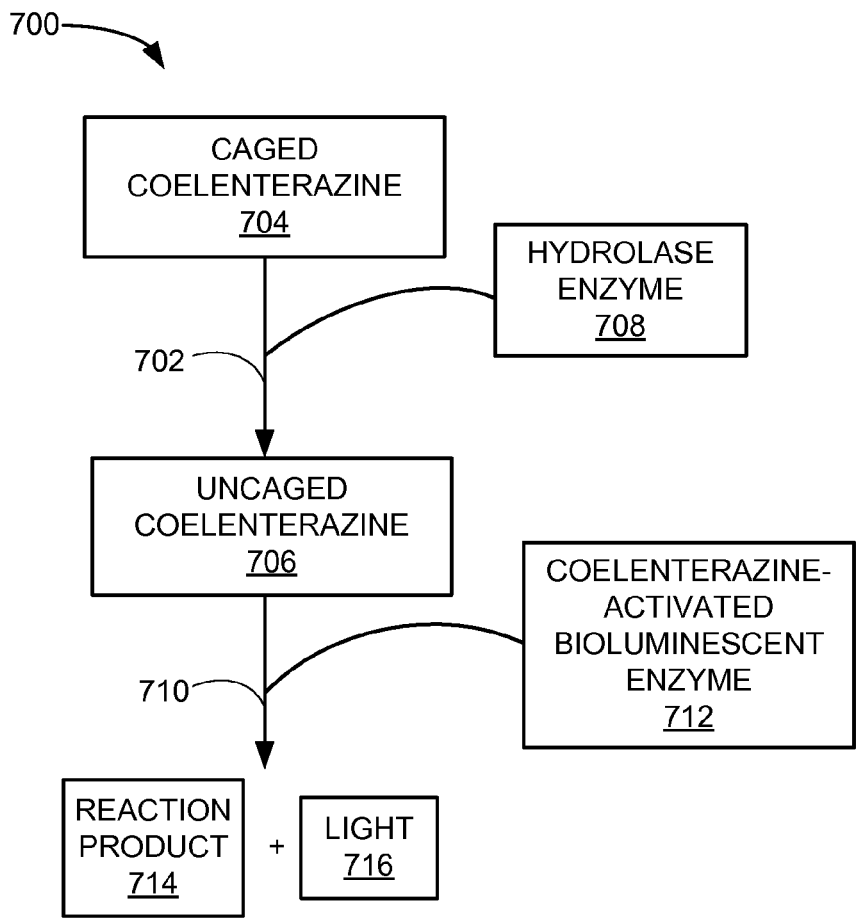
FIG. 7 is a reaction diagram of a generalized assay for hydrolase activity, in another embodiment of the present invention.

Referring now to FIG. 7, therein is shown a reaction diagram of a generalized assay for hydrolase activity 700, in another embodiment of the present invention. The reaction diagram of the generalized assay for hydrolase activity 700 depicts a hydrolysis reaction 702 wherein a caged coelenterazine molecule 704 is converted into an uncaged coelenterazine molecule 706 by the hydrolysis reaction 702 catalyzed by a hydrolase enzyme 708, which can cleave a caging group from the caged coelenterazine molecule 704, forming the uncaged coelenterazine molecule 706.

The reaction diagram of the generalized assay for hydrolase activity 700 further depicts the uncaged coelenterazine molecule 706 in a bioluminescence reaction 710 catalyzed by a coelenterazine-activated bioluminescent enzyme 712. The bioluminescence reaction 710 produces a reaction product 714 and a light emission 716. Detection of the light emission 716 provides a qualitative and quantitative measure of the activity of the hydrolase enzyme 708. The caged coelenterazine molecule 704 is not active or is minimally active as a substrate for the bioluminescence reaction 710.

The term "hydrolase enzyme" as used herein is defined as an enzyme that catalyzes the hydrolysis of a carbon-nitrogen, carbon-oxygen, phosphorous-nitrogen, and phosphorous-oxygen chemical bonds. Examples of bonds cleaved by hydrolases include but are not limited to amide bonds including cyclic amide bonds, ester bonds including cyclic ester bonds, phosphoramide bonds, and phosphates. Examples of hydrolase enzymes include but are not limited to peptidases, proteases, esterases, glycosylases, and ether hydrolases. Beta-lactamase is one example of an enzyme that catalyzes the hydrolysis of a cyclic amide bond.

The term "coelenterazine-activated bioluminescent enzyme" as used herein is defined as a bioluminescent enzyme that employs a coelenterazine molecule or one of its derivatives as a substrate for catalyzing bioluminescence. *Renilla* luciferase, *Gaussia* luciferase, *Oplophorus* luciferase and their synthetic mutants are examples of coelenterazine-activated bioluminescent enzymes. Synthetic coelenterazine-activated bioluminescent enzymes may be produced using recombinant protein expression techniques. Luc8 is an example of a mutant of *Renilla* luciferase and NanoLuc is an example of an engineered luciferase derived from *Oplophorus* luciferase.

Figure 8:
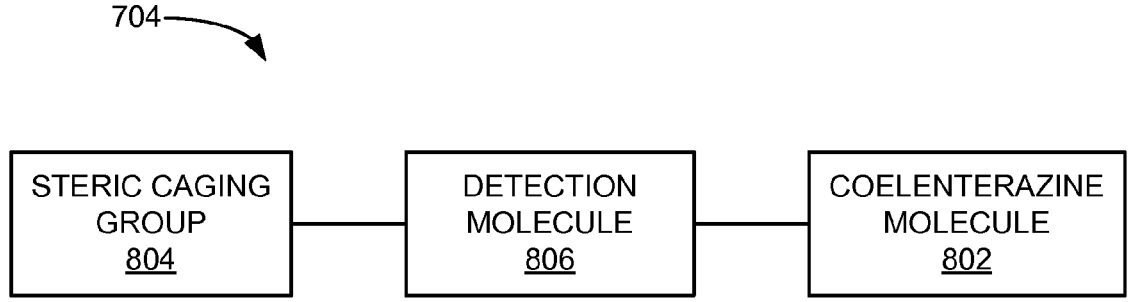
FIG. 8 is a schematic diagram of the caged coelenterazine molecule of FIG. 7.

Referring now to FIG. 8 therein is shown a schematic diagram of the caged coelenterazine molecule 704 of FIG. 7. The caged coelenterazine molecule 704 includes a coelenterazine molecule 802 and a steric caging group 804. A detection molecule 806 is positioned between the coelenterazine molecule 802 and the steric caging group 804. The coelenterazine molecule 802 is bonded to the detection molecule 806 which is bonded to the steric caging group 804.

It has been discovered that the steric caging group 804 in conjunction with the detection molecule 806 allows for more effective reduction in the bioluminescent properties of the coelenterazine molecule 802. The detection molecule 806 by itself is not an effective caging molecule for reducing the bioluminescent activity of the coelenterazine molecule 802, but when attached the steric caging group 804, easy detection with effective suppression of the coelenterazine molecule 802 is achieved.

The term "coelenterazine molecule" as used herein is defined as any molecule containing a coelenterazine imisazopyrazinone core structure. Examples of coelenterazines include but are not limited to native coelenterazine, coelenterazine-h, coelenterazine fluoro, and coelenterazine analogs such as furimazine and its derivatives.

The term "detection molecule" as used herein is defined as the chemical motif recognized by the hydrolase enzyme. Examples of detection molecules include but are not limited to peptides and beta-lactam groups.

The term "steric caging group" as used herein is defined as sugars and synthetic polymers designed to hinder binding access of the caged coelenterazine to the active pocket of the coelenterazine-activated bioluminescent enzyme. Examples of steric caging groups include but are not limited to cyclodextrins, dextrans, polyethylene glycols, polystyrene, and polylysine. In general, the steric caging group is relatively large so as to physically inhibit binding between the caged coelenterazine and the coelenterazine-activated bioluminescent enzyme. In an alternate embodiment of this invention, the term "steric caging group" includes a solid support such as a material surface or the surface of a solid phase material such as dextran, glass, and polystyrene beads.

Figure 9:
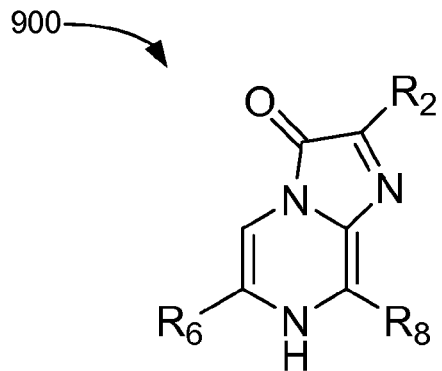
FIG. 9 is a coelenterazine imisazopyrazinone core structure.

Referring now to FIG. 9 therein is shown a coelenterazine imisazopyrazinone core structure 900. As has been defined above, any molecule containing the coelenterazine imisazopyrazinone core structure 900 can be considered a coelenterazine molecule. The R groups are numbered according to the numbering system of the ring atoms in the imisazopyrazinone core structure and can be any suitable chemical group, atom, or molecule.

Figure 10:
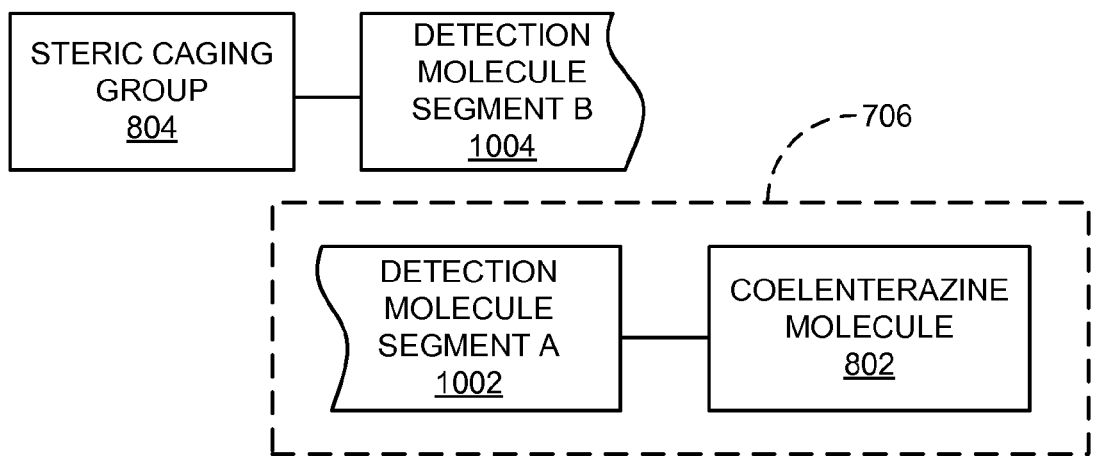
FIG. 10 is a schematic diagram of the uncaged coelenterazine molecule of FIG. 7.

Referring now to FIG. 10 therein is shown a schematic diagram of the uncaged coelenterazine molecule 706 of FIG. 7. The uncaged coelenterazine molecule 706 is activated by the hydrolysis reaction 702 of FIG. 7 catalyzed by the hydrolase enzyme 708 of FIG. 7 acting on the detection molecule 806 of FIG. 8. The hydrolysis reaction 702 cleaves the detection molecule 806 into a detection molecule segment A 1002 attached to the coelenterazine molecule 802 and a detection molecule segment B 1004 attached to the steric caging group 804.

The uncaged coelenterazine molecule 706 of FIG. 7 thus includes the detection molecule segment A 1002 and the coelenterazine molecule 802. The presence of the detection molecule segment A 1002 may alter the properties of the coelenterazine molecule 802 but does not decrease the activity of the uncaged coelenterazine molecule 706 close to background levels, enabling quantitative and qualitative detection of the uncaged coelenterazine molecule 706. In an embodiment of this invention, the hydrolysis reaction 702 cleaves the detection molecule 806 entirely from the coelenterazine molecule 802 such that the detection molecule segment A 1002 is not attached to the coelenterazine molecule 802.

Figure 11:
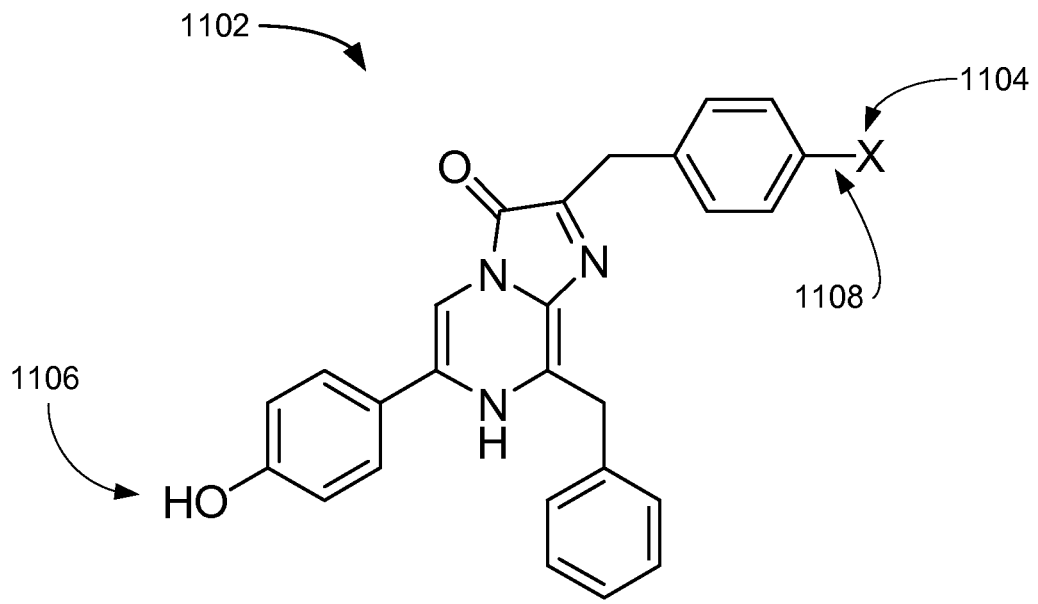
FIG. 11 is a coelenterazine derivative in a first embodiment of the coelenterazine molecule of FIG. 8.

Referring now to FIG. 11 therein is shown a coelenterazine derivative 1102 in a first embodiment of the coelenterazine molecule 802 of FIG. 8. A side group X 1104 defines the type of the coelenterazine derivative 1102. When the side group X 1104 is a hydroxyl group the coelenterazine derivative 1102 is a native coelenterazine. If the side group X 1104 is a hydrogen, the coelenterazine derivative 1102 is coelenterazine-h. The side group X 1104 as a fluorine defines the coelenterazine derivative 1102 as a fluoro coelenterazine. The detection molecule 806 of FIG. 8 may be attached to a first bonding site 1106 or a second bonding site 1108.

Figure 12:
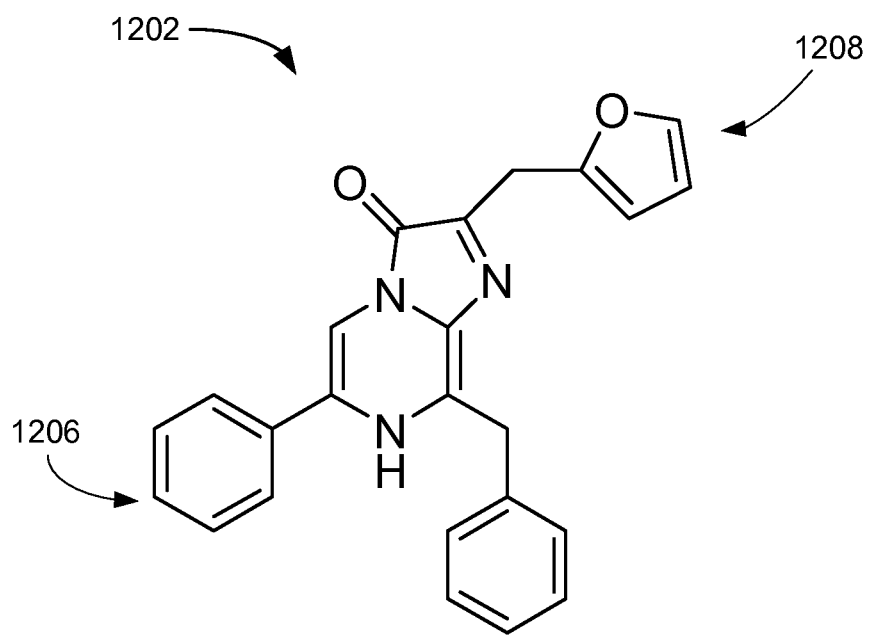
FIG. 12 is a furimazine, a coelenterazine analog, in a second embodiment of the coelenterazine molecule of FIG. 8.

Referring now to FIG. 12 therein is shown a furimazine 1202, a coelenterazine analog, in a second embodiment of the coelenterazine molecule 802 of FIG. 8. The detection molecule 806 of FIG. 8 may be attached to a first bonding site 1206 or a second bonding site 1208. The first bonding site 1206 can be a hydroxyl group attached at the location of the first bonding site 1206, for example.

Figure 13:
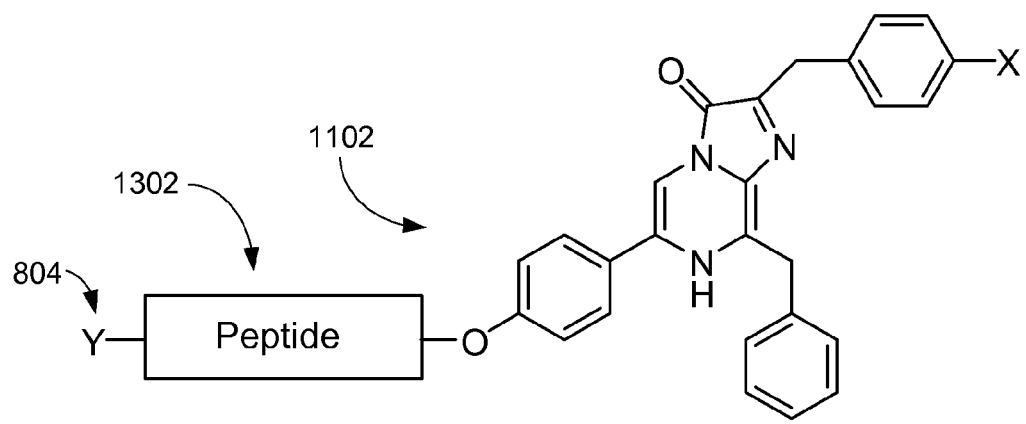
FIG. 13 is the coelenterazine derivative and a peptide in a first embodiment of the caged coelenterazine molecule of FIG. 7 and FIG. 8.

Referring now to FIG. 13 therein is shown the coelenterazine derivative 1102 and a peptide 1302 in a first embodiment of the caged coelenterazine molecule 704 of FIG. 7 and FIG. 8. In this embodiment, the detection molecule 806 of FIG. 8 is the peptide 1302. Also shown is the steric caging group 804 as the letter Y bonded to the peptide 1302.

Figure 14:
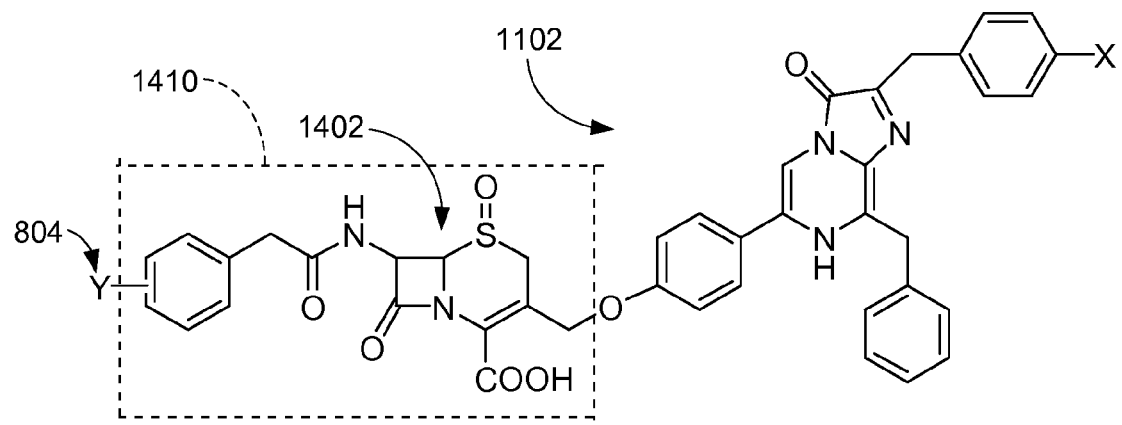
FIG. 14 is the coelenterazine derivative and a beta-lactamase substrate in a second embodiment of the caged coelenterazine molecule of FIG. 7 and FIG. 8.

Referring now to FIG. 14 therein is shown the coelenterazine derivative 1102 and a beta-lactamase substrate 1410 in a second embodiment of the caged coelenterazine molecule 704 of FIG. 7 and FIG. 8. In this embodiment, the detection molecule 806 of FIG. 8 is the beta-lactamase substrate 1410 having a beta-lactam group 1402 can also be called cephalosporin. The beta-lactamase substrate 1410 is bounded by the dotted rectangle. The beta-lactam group 1402 is the four-membered carbon ring fused to the six-membered ring within the beta-lactamase substrate 1410. Also shown is the steric caging group 804 as the letter Y bonded to the beta-lactamase substrate 1410.

The term "beta-lactamase substrate" as used herein is defined as any chemical motif that is a substrate for a beta-lactamase enzyme. Examples of beta-lactamase substrates include but are not limited to penicillins, cephamycins, and carbapenems.

Figure 15:
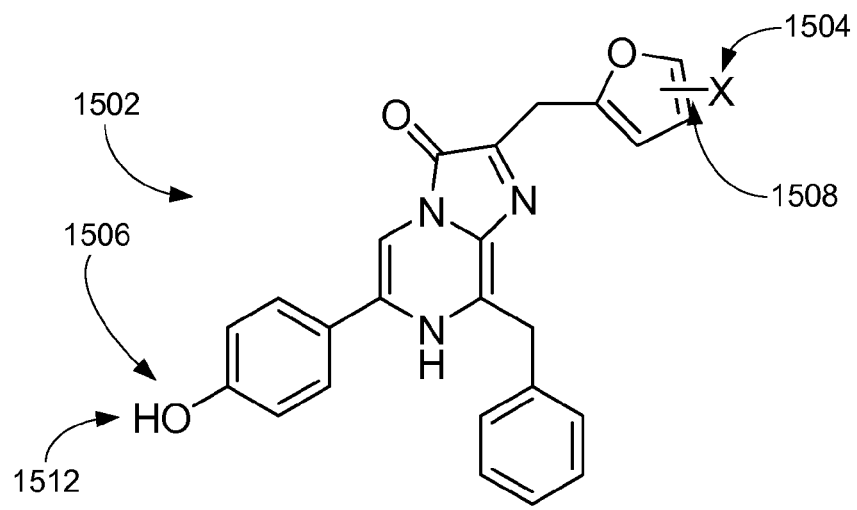
FIG. 15 is a furimazine derivative and a hydroxyl group in a third embodiment of the coelenterazine molecule of FIG. 8.

Referring now to FIG. 15 therein is shown a furimazine derivative 1502 and a hydroxyl group 1512 in a third embodiment of the coelenterazine molecule 802 of FIG. 8. The furimazine derivative 1502 has the hydroxyl group 1512 bonded to a first bonding site 1506. A side group X 1504 defines the type of the furimazine derivative 1502 in a similar manner as the side group X 1104 of FIG. 11 defines the type of the coelenterazine derivative 1102 of FIG. 11. The side group X 1504 is shown with a bond between two bonds in a ring structure in order to show that the side group X 1504 may be attached or bonded to any of the ring carbon atoms that are available for attachment. The side group X 1504 may be a second bonding site 1508.

Figure 16:
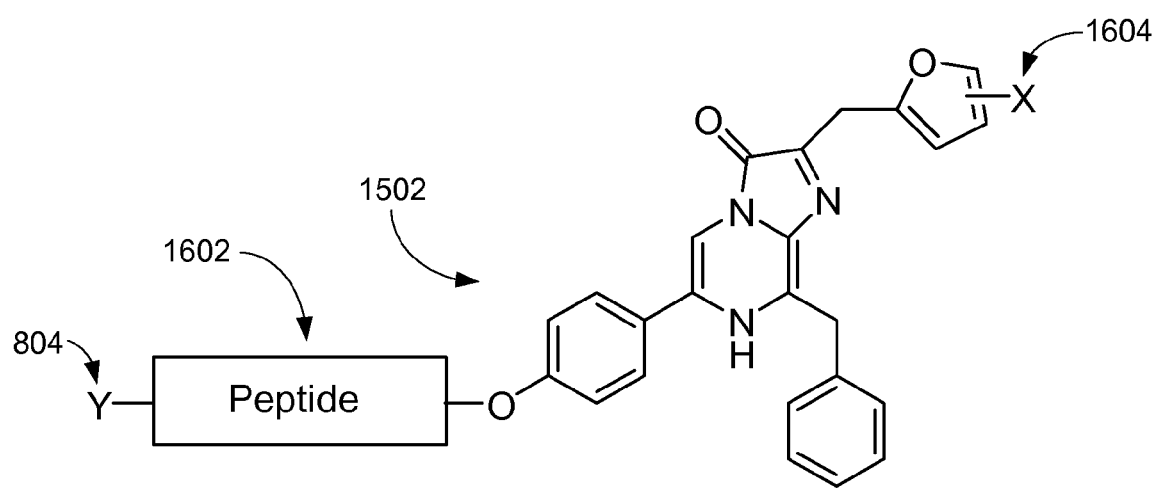
FIG. 16 is the furimazine derivative and a peptide in a third embodiment of the caged coelenterazine molecule of FIG. 7 and FIG. 8.

Referring now to FIG. 16 therein is shown the furimazine derivative 1502 and a peptide 1602 in a third embodiment of the caged coelenterazine molecule 704 of FIG. 7 and FIG. 8. In this embodiment, the detection molecule 806 of FIG. 8 is the peptide 1602. The peptide 1602 can be bonded to the furimazine derivative 1502 through reaction with the hydroxyl group 1512 of FIG. 15, for example. Also shown is the steric caging group 804 as the letter Y bonded to the peptide 1602. A side group X 1604 defines the type of the furimazine derivative 1502 in a similar manner as the side group X 1104 of FIG. 11 defines the type of the coelenterazine derivative 1102 of FIG. 11. The side group X 1604 is shown with a bond between two bonds in a ring structure in order to show that the side group X 1604 may be attached or bonded to any of the ring carbon atoms that are available for attachment.

The peptide 1602 is shown as the detection molecule 806, but it is understood that other structures can be used. For example, the detection molecule 806 could be the beta-lactamase substrate 1410 of FIG. 14 having the beta-lactam group 1402 of FIG. 14, and could be detected using a hydrolase such as beta-lactamase.

It has been discovered that the use of the furimazine derivative 1502 in conjunction with the peptide 1602 or other structures as the detection molecule 806 along with the steric caging group 804 allows for easier detection of the hydrolase enzyme 708. The furimazine derivative 1502 has been found to be strongly selective for new forms of luciferase such as NanoLuc, resulting in greater light output at the same concentration as other coelenterazine derivatives. At the same time, the steric caging group 804 ensures that the caged coelenterazine molecule 704 will be effectively suppressed before activation by the hydrolase enzyme, ensuring an accurate measurement of the amount of the hydrolase enzyme present.

While the invention has been described in conjunction with a specific best mode, it is to be understood that many alternatives, modifications, and variations will be apparent to those skilled in the art in light of the aforegoing description. Accordingly, it is intended to embrace all such alternatives, modifications, and variations that fall within the scope of the included claims. All matters hithertofore set forth herein or shown in the accompanying drawings are to be interpreted in an illustrative and non-limiting sense.

What is claimed is:

1. A qualitative and quantitative hydrolase detection method comprising:
providing a caged coelenterazine molecule having a detection molecule which is a hydrolase substrate having an amide bond or an ester bond capable of cleavage by a hydrolase bonded between a first bonding site or a second bonding site of a coelenterazine molecule and a steric caging group, the steric caging group selected from the group consisting of sugars, synthetic polymers, or a solid support structure large enough to physically inhibit bonding to the caged coelenterazine molecule;
activating an uncaged coelenterazine molecule by cleaving the detection molecule in the caged coelenterazine molecule with a hydrolase enzyme;
determining a light emission from a coelenterazine-activated bioluminescent enzyme reacting with the uncaged coelenterazine molecule activated in the presence of the hydrolase enzyme, the coelenterazine-activated bioluminescent enzyme selected from the group consisting of *Renilla* luciferase, *Gaussia* luciferase, *Oplophorus* luciferase, or their synthetic mutants; and
correlating the light emission for quantitatively and qualitatively determining the presence of the hydrolase enzyme.

2. The method as claimed in claim 1 wherein providing the caged coelenterazine molecule having the detection molecule includes providing the caged coelenterazine molecule having a peptide.

3. The method as claimed in claim 1 wherein providing the caged coelenterazine molecule having the detection molecule includes providing the caged coelenterazine molecule having a beta-lactamase substrate.

4. The method as claimed in claim 1 wherein providing the caged coelenterazine molecule having the coelenterazine molecule includes providing the caged coelenterazine molecule having a coelenterazine derivative.

5. The method as claimed in claim 1 wherein providing the caged coelenterazine molecule having the coelenterazine molecule includes providing the caged coelenterazine molecule having a furimazine derivative.

6. A qualitative and quantitative hydrolase detection composition comprising:
a caged coelenterazine molecule having a detection molecule which is a hydrolase substrate having an amide bond or an ester bond capable of cleavage by a hydrolase bonded between a first bonding site or a second bonding site of a coelenterazine molecule and a steric caging group, the steric caging group selected from the group consisting of sugars, synthetic polymers, or a solid support structure large enough to physically inhibit bonding to the caged coelenterazine molecule;
a hydrolase enzyme for activating an uncaged coelenterazine molecule by cleaving the detection molecule in the caged coelenterazine molecule for releasing the steric caging group bonded to the detection molecule with the hydrolase enzyme; and
a coelenterazine-activated bioluminescent enzyme for detecting the hydrolase enzyme based on correlating a light emission from the coelenterazine-activated bioluminescent enzyme reacted with the uncaged coelenterazine molecule activated in the presence of the hydrolase enzyme for quantitatively and qualitatively determining the presence of the hydrolase enzyme, the coelenterazine-activated bioluminescent enzyme selected from the group consisting of *Renilla* luciferase, *Gaussia* luciferase, *Oplophorus* luciferase, or their synthetic mutants.

7. The composition as claimed in claim 6 wherein the detection molecule is a peptide.

8. The composition as claimed in claim 6 wherein the detection molecule is a beta-lactamase substrate.

9. The composition as claimed in claim 6 wherein the coelenterazine molecule is a coelenterazine derivative.

10. The composition as claimed in claim 6 wherein the coelenterazine molecule is a furimazine derivative.

11. The composition as claimed in claim 6 wherein:
the light emission correlates to the amount of the hydrolase enzyme; and
the detection molecule is a peptide.

12. The composition as claimed in claim 11 wherein the hydrolase enzyme is a peptidase.

13. The composition as claimed in claim 11 wherein the hydrolase enzyme is a protease.

14. The composition as claimed in claim 11 wherein the peptide is bonded to cyclodextrin.

15. The composition as claimed in claim 11 wherein the peptide is bonded to polyethylene glycol.

16. A qualitative and quantitative hydrolase detection method comprising:
providing a caged coelenterazine molecule having a peptide as a detection molecule which is a hydrolase substrate having an amide bond or an ester bond capable of cleavage by a hydrolase bonded between a first bonding site or a second bonding site of a coelenterazine molecule and a steric caging group, the steric caging group selected from the group consisting of sugars, synthetic polymers, or a solid support structure large enough to physically inhibit bonding to the caged coelenterazine molecule;
activating an uncaged coelenterazine molecule by cleaving the peptide in the caged coelenterazine molecule with a hydrolase enzyme which separates the steric caging group from the coelenterazine molecule;
determining a light emission from a coelenterazine-activated bioluminescent enzyme reacting with the uncaged coelenterazine molecule activated in the presence of the hydrolase enzyme, the coelenterazine-activated bioluminescent enzyme selected from the group consisting of *Renilla* luciferase, *Gaussia* luciferase, *Oplophorus* luciferase, or their synthetic mutants; and
correlating the light emission for quantitatively and qualitatively determining the presence of the hydrolase enzyme.

17. The method as claimed in claim 16 further comprising detecting a peptidase.

18. The method as claimed in claim 16 further comprising detecting a protease.

19. The method as claimed in claim 16 wherein providing the caged coelenterazine molecule having the steric caging group includes providing the caged coelenterazine molecule having cyclodextrin.

20. The method as claimed in claim 16 wherein providing the caged coelenterazine molecule having the steric caging group includes providing the caged coelenterazine molecule having polyethylene glycol.

* * * * *